(12) United States Patent
Ng et al.

(10) Patent No.: US 10,098,580 B2
(45) Date of Patent: Oct. 16, 2018

(54) HYPERMOTOR ACTIVITY DETECTION SYSTEM AND METHOD THEREFROM

(71) Applicants: Agency for Science, Technology and Research, Singapore (SG); Singapore Health Services Pte Ltd, Singapore (SG)

(72) Inventors: Ee Sin Ng, Singapore (SG); How Lung Eng, Singapore (SG); Wei Shih Derrick Chan, Singapore (SG); That Mon Htwe, Singapore (SG); Wiriyanto Darsono, Singapore (SG)

(73) Assignees: Agency for Science, Technology and Research, Singapore (SG); Singapore Health Service Pte Ltd, Singapore (SG)

( * ) Notice: Subject to any disclaimer, the term of this patent is extended or adjusted under 35 U.S.C. 154(b) by 0 days.

(21) Appl. No.: 15/037,791

(22) PCT Filed: Nov. 19, 2014

(86) PCT No.: PCT/SG2014/000547
§ 371 (c)(1),
(2) Date: May 19, 2016

(87) PCT Pub. No.: WO2015/076752
PCT Pub. Date: May 28, 2015

(65) Prior Publication Data
US 2016/0302714 A1    Oct. 20, 2016

(30) Foreign Application Priority Data
Nov. 19, 2013 (SG) ................ 201308535-2

(51) Int. Cl.
*A61B 5/00* (2006.01)
*A61B 5/11* (2006.01)
(Continued)

(52) U.S. Cl.
CPC .......... *A61B 5/4094* (2013.01); *A61B 5/0077* (2013.01); *A61B 5/1118* (2013.01);
(Continued)

(58) Field of Classification Search
CPC ......................... G06K 9/00335; A61B 5/0077
See application file for complete search history.

(56) References Cited

U.S. PATENT DOCUMENTS

2012/0053491 A1    3/2012 Nathan et al.

OTHER PUBLICATIONS

Cuppens, et al., Automatic Video Detection of Body Movement During Sleep Based on Optical Flow in Pediatric Patients with Epilepsy, 48 Med Biol Eng Comput 923 (Jun. 2010).
(Continued)

*Primary Examiner* — Carl H Layno
*Assistant Examiner* — Jennifer Ghand
(74) *Attorney, Agent, or Firm* — Womble Bond Dickinson (US) LLP (57) ABSTRACT

There is provided a hypermotor activity detection system, including: a video capture device configured to monitor a patient and obtain a video input; and a processing system configured to process the video input. The processing system includes: an optical flow module configured to carry out an optical flow analysis on a video input region determined from the video input, and further determine a flow field magnitude of the video input region; and a local motion reference module configured to obtain a local motion reference value. The local reference module includes: a division module; a sub-window flow module; a local motion magnitude module; and a local motion comparison module. Further, a corresponding method for detecting hypermotor activity is provided.

23 Claims, 6 Drawing Sheets

(51) Int. Cl.
*G06K 9/00* (2006.01)
*H04N 5/232* (2006.01)
*G06T 7/215* (2017.01)
*G06T 7/246* (2017.01)
*G06T 7/269* (2017.01)

(52) U.S. Cl.
CPC ........ *A61B 5/1128* (2013.01); *G06K 9/00335* (2013.01); *G06T 7/215* (2017.01); *G06T 7/246* (2017.01); *G06T 7/269* (2017.01); *H04N 5/232* (2013.01); *G06T 2207/20021* (2013.01)

(56) References Cited

OTHER PUBLICATIONS

Karayiannis, et al., Quantifying Motion in Video Recordings of Neonatal Seizures by Regularized Optical Flow Methods, 14 IEEE Transactions on Image Processing 890 (Jul. 2005).

Pediaditis, et al. Exploiting Advanced Video Analysis Technologies for a Smart Home Monitoring Platform for Epileptic Patients: Technological and Legal Preconditions, International Conference on Telecommunications and Multimedia (TEMU) 202 (2012).

HYPERMOTOR ACTIVITY DETECTION SYSTEM AND METHOD THEREFROM

CROSS-REFERENCE TO RELATED APPLICATIONS

The present application claims the benefit of Singapore patent application no. 201308535-2, filed on 19 Nov. 2013, the entire contents of which are incorporated herein by reference for all purposes.

TECHNICAL FIELD

The present disclosure describes embodiments generally relating to a method of detecting hypermotor activity. In embodiments, the method can be applied as a video analytics solution in detecting hypermotor activity. Further, a hypermotor activity detection system is provided.

INTRODUCTION

Epilepsy and seizures warrant significant attention since they are medical conditions which affect a significant proportion of the world's population. According to the World Health Organisation (WHO), more than 50 million people worldwide have epilepsy. More importantly, pediatric patients with epilepsy commonly have nocturnal seizures intermittently and unpredictably, necessitating constant monitoring by parents or Caregivers while they sleep.

In particular, hypermotor seizures, which are a subset of seizures associated with patients with epilepsy can be considered to be extremely dangerous, as epileptic patients would temporarily be in an uncontrollable physical state characterized by large and persistent motions, and are in danger of accidents resulting from such seizures and which can even lead to cases of sudden unexplained deaths in epilepsy (SUDEP). SUDEP accounted for approximately 8-17% of deaths in people with epilepsy. Thus, the monitoring and detection of hypermotor seizures can be considered as extremely important.

The standard approach for monitoring patients with seizures in hospital involves the use of electro-encephalography (EEG) in hospitals. Typically, a video of the patient is also captured through epilepsy monitoring units (EMUs) for analysis by clinicians. By analyzing EEG data along with the captured video, clinicians can identify and verify the occurrences of seizures. There are several challenging issues with such an approach of monitoring. Firstly, reviewing recorded video data is tedious and challenging, and there typically would be many long hours of video data available. As such, it may be difficult to accurately identify periods of hypermotor seizures. Secondly, such monitoring is typically performed under supervised conditions, where a caregiver is present to trigger an alarm when seizures occur. Thus, this relies heavily on the alertness of the caregiver, which could be affected under prolonged periods of supervised monitoring.

Lastly, it is not feasible to extend this approach of monitoring patients with seizures as a home-based long-term solution. EEG requires trained technologists to operate and analyze, and it can be considered as impractical to require constant supervised monitoring of patients at home.

It is thus desired for a video analytics system for general and non-invasive monitoring of epileptic patients, and capable of providing constant supervised monitoring of epileptic patients, especially when they sleep.

SUMMARY

According to various embodiments in the present disclosure, there is provided a hypermotor activity detection system, including: a video capture device configured to monitor a patient and obtain a video input; and a processing system configured to process the video input, including: a optical flow module configured to carry out an optical flow analysis on a video input region determined from the video input, and further determine a flow field magnitude of the video input region; a local motion reference module including: a division module configured to divide the video input region into a plurality of sub-windows; a sub window flow module configured to determine a sub-window flow field magnitude for each of the plurality of sub-windows; a local motion magnitude module configured to obtain a magnitude of local motion based on the sub-window flow field magnitude for each of the plurality of sub-windows; and a local motion comparison module configured to compare the magnitude of local motion with a local motion threshold for a predetermined number of observation frames to obtain a local motion reference value.

According to various embodiments in the present disclosure, there is provided a method for detecting hypermotor activity, the method including: carrying out an optical flow analysis on a video input region, including determining a flow field magnitude of the video input region; dividing the video input region into a plurality of sub-windows; determining a sub-window flow field magnitude for each of the plurality of sub-windows; and obtaining a magnitude of local motion based on the sub-window flow field magnitude for each of the plurality of sub-windows; and comparing the magnitude of local motion with a local motion threshold for a predetermined number of observation frames to obtain a local motion reference value.

According to various embodiments in the present disclosure, there is provided a computer program readable medium having a program recorded thereon, wherein the program is executed to make a computer carry out a method for detecting hypermotor activity.

BRIEF DESCRIPTION OF THE DRAWINGS

In the drawings, like reference characters generally refer to the same parts throughout the different views. The drawings are not necessarily to scale, with emphasis instead generally being placed upon illustrating the principles of the present disclosure. It is to be noted that the accompanying drawings illustrate only examples of embodiments of this disclosure and are therefore not to be considered limiting of its scope, for the disclosure may admit to other equally effective embodiments. In the following description, various embodiments of the disclosure are described with reference to the following drawings, in which.

DETAILED DESCRIPTION

Embodiments of a method of detecting hypermotor activity and a hypermotor activity detection system are described in detail below with reference to the accompanying figures. However, it should be understood that the disclosure is not limited to specific described embodiments. It will be appreciated that the embodiments described below can be modified in various aspects, features, and elements, without changing the essence of the disclosure. Further, any reference to various embodiments shall not be construed as a generalization of any inventive subject matter disclosed herein and shall not be considered to be an element or limitation of the appended claims except where explicitly recited in a claim(s).

According to various embodiments, depiction of a given element or consideration or use of a particular element number in a particular FIG. or a reference thereto in corresponding descriptive material can encompass the same, an equivalent, or an analogous element or element number identified in another FIG. or descriptive material associated therewith. The use of "/" herein means "and/or" unless specifically indicated otherwise.

The present disclosure can describe embodiments of a system or apparatus which can be operable in various orientations, and it thus should be understood that any of the terms "top", "bottom", "base", "down", "sideways", "downwards" etc., when used in the following description are used for convenience and to aid understanding of relative positions or directions, and not intended to limit the orientation of a system or apparatus.

In embodiments, the system may include a memory which is for example used in the processing carried out by the system. A memory used in the embodiments may be a volatile memory, for example a DRAM (Dynamic Random Access Memory) or a non-volatile memory, for example a PROM (Programmable Read Only Memory), an EPROM (Erasable PROM), EEPROM (Electrically Erasable PROM), or a flash memory, e.g., a floating gate memory, a charge trapping memory, an MRAM (Magnetoresistive Random Access Memory) or a PCRAM (Phase Change Random Access Memory).

In an embodiment, a "circuit" or a "module" may be understood as any kind of a logic implementing entity, which may be special purpose circuitry or a processor executing software stored in a memory, firmware, or any combination thereof. Thus, in an embodiment, a "circuit" or a "module" may be a hard-wired logic circuit or a programmable logic circuit such as a programmable processor, e.g. a microprocessor (e.g. a Complex Instruction Set Computer (CISC) processor or a Reduced Instruction Set Computer (RISC) processor). A "circuit" or a "module" may also be a processor executing software, e.g. any kind of computer program, e.g. a computer program using a virtual machine code such as e.g. Java. Any other kind of implementation of the respective functions which will be described in more detail below may also be understood as a "circuit" or a "module" in accordance with an alternative embodiment.

Prior to discussion of embodiments of the present disclosure, reference is made to representative systems which are available in seeking to address an objective of providing constant monitoring of epileptic patients. Various available methods are directed to the use of video data for detecting epileptic seizures. In general, such methods can be divided into two distinct categories.

A first category can be that of marker-based systems, which typically rely on physical markers such as infra-red markers and colored pajamas worn by patients to track and analyze the movement of the patients.

Generally, marker-based systems allow for the interpretation and identification of seizures in epileptic patients through the analysis and recognition of key features from patients' motions. However, marker-based systems typically require a calibrated system in a highly controlled environment, such as the use of infra-red sensors, reflectors and markers, which may not be suitable for extended monitoring of patients in homes. The performance of marker-based systems may also affected by issues such as self-occlusion and tracking reliability.

A second category can include marker-less systems, which rely on techniques such as optical flow analysis, change detection and block matching to detect, analyze and recognize the motion of patients. Such systems can further be sub-categorized to three main groups based on the functionality of the proposed systems.

A first group can be for the systems that detect epileptic seizures based on motion detection. These systems are generally designed for intelligent monitoring of patients and to detect epileptic seizures reliably and automatically, without specific consideration for the analysis and recognition of seizures.

A second group can be for the systems that detect epileptic seizures while analyzing the seizures based on motion analysis. These systems extract information on the intrinsic characteristics of seizures based on patients' movements to aid in analysis and diagnosis.

A third group can be for systems that detect and identify specific seizure types through motion recognition. These systems are designed to differentiate between seizures and natural movements of patients, and to identify the type of seizure which has occurred through a learning algorithm.

In embodiments of the present disclosure, video data is exploited for detecting hypermotor seizures. Such a system according to embodiments is designed to provide intelligent monitoring of patients in hospitals and homes. Advantageously, the system is able to detect seizures automatically and reliably in unsupervised conditions. Accordingly, embodiments of the present disclosure can be considered to adopt a marker-less approach in the providing a system for the detection of hypermotor activities. As embodiments seek to provide a long-term monitoring solution to detect seizures and capture video clips for post-analysis by clinicians, it may be considered relevant to the category of motion detection.

Current clinical alternatives only detect generalized convulsive seizures, are not in widespread use and have shortcomings. For example, multimodal seizure alarms may have poor sensitivity and are poorly tolerated, accelerometer-based movement detection alarms may be difficult to use consistently in children, and pressure pad-based systems may have limited utility in non-tonic-clonic seizures. Generally, none of the current modalities seem to be able to clarify a diagnosis of epilepsy. As such, better ways to evaluate nocturnal events and discern which events require detailed investigation are required.

Prior work on seizure detection based on motion detection include a marker-less motion detection algorithm which detects epileptic seizures during sleep based on the optical flow analysis of pediatric patients. When significant body movements are present, the flow magnitude would be large and the algorithm triggers a detection.

In the above detection algorithm, only pixels with the largest flow magnitude were considered for detecting hypermotor seizures. However, such a consideration does not result in accurate detections, as considering only pixels with largest flow magnitude would lead to more false alarms being set off, due to the monitoring of body movements of patients not caused by epileptic seizures. Nevertheless, such an algorithm supports an approach of utilizing optical flow in analyzing video data.

According to various embodiments in the present disclosure, there is provided a hypermotor activity detection system, including: a video capture device configured to monitor a patient and obtain a video input; and a processing system configured to process the video input, including: a optical flow module configured to carry out an optical flow analysis on a video input region determined from the video input, and further determine a flow field magnitude of the video input region; a local motion reference module including: a division module configured to divide the video input region into a plurality of sub-windows; a sub-window flow module configured to determine a sub-window flow field magnitude for each of the plurality of sub-windows; a local motion magnitude module configured to obtain a magnitude of local motion based on the sub-window flow field magnitude for each of the plurality of sub-windows; and a local motion comparison module configured to compare the magnitude of local motion with a local motion threshold for a predetermined number of observation frames to obtain a local motion reference value.

Such a system and corresponding method provides a video analytics system for general monitoring of patients. The system according to various embodiments is non-invasive and does not require any wearable devices. Such a system is designed to be a standalone system, which can be deployed in hospitals and also in homes as a long-term intelligent monitoring solution. Hardware installation is kept to a minimum, and the system only requires a camera with low lux capability, for night-time observation. Further, the system is able to detect seizures automatically and reliably in unsupervised conditions. Upon detection of hypermotor activities, the system alerts the caregiver, and records the video for post-analysis by clinicians.

According to various embodiments, a method and system for detecting hypermotor activities include the consideration of regions with persistent local motion in addition to monitoring global motion in detecting hypermotor seizures. Identifying the persistence of local motion has been identified by the present inventors as essential for accurate detections. Extensive testing on over 200 hours of patient video data has shown that the proposed system achieves reliable and accurate performance.

The technical basis of providing for and carrying out a system and method for detecting hypermotor activity is now discussed.

Figure 1:
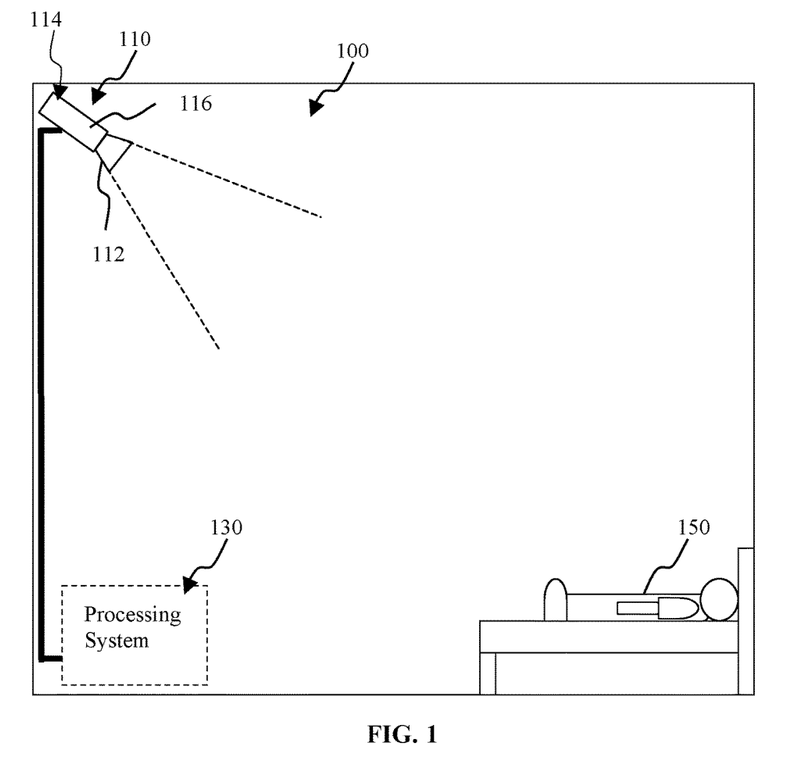
FIG. 1 illustrates a system arranged for detecting hypermotor activity according to embodiments of the present disclosure.

FIG. 1 illustrates a system arranged for detecting hypermotor activity according to embodiments of the present disclosure. System 100 is provided, for supervisory monitoring non-invasive monitoring of a patient. System 100 can be a hypermotor activity detection system 100. In such case, a patient 150, possibly one with a prior diagnosis of epilepsy and prone to or having a likelihood of suffering an epileptic seizure, can be monitored by way of system 100. Minimally, system 100 only requires a video capture device or a camera 110 for monitoring the patient 150.

Camera 110 can be a device capable of recording optical information of a target through an optical lens arrangement 112. The optical lens arrangement 112 can be adjusted to obtain clear focus on the target patient 150. Focus can be carried out manually, remotely, or with an automatic function. Images received through the optical lens arrangement are thereafter converted into digital information in the processing unit 114 of the camera 110, which can be contained in the camera body 116. Optical recording resolution of the camera 100 can be provided as sufficient for such a monitoring function.

Camera 110 can be mounted on a structural wall or in an elevated position, to provide unblocked observation fields and with clear vision of the patient. In embodiments, the system 100 is provided for day-time monitoring of the patient 150. Camera 110 can be mounted in a day activity room, a kitchen, a bedroom, a hospital ward, a hospital patient's room, a hospital ward corridor, or any other location for which a patient can be expected to spend time or could experience a seizure at. In embodiments, the camera 110 is provided with a view capture area. In other embodiments, camera 110 can be rotated. In embodiments, system 100 can include a mobile camera mounted on a ceiling track, and provided with visual tracking capability, so as to follow a patient around a home or any other environment, for persistent non-invasive monitoring for seizure episodes.

The camera 110 can be mounted or affixed to a structural element such as to provide a fixed point of view of a room in which a patient resides. The camera 110 can be a camera capable of low light operation and can include a low lux rated camera. In embodiments, the camera can be a night vision enabled camera, and can have infrared illuminators for night time operation. In embodiments, the camera can include near infra-red capability. Captured imaging converted to digital information in the processing unit 114 of the camera 110 can be provided to a processing system 130 for processing.

Figure 2:
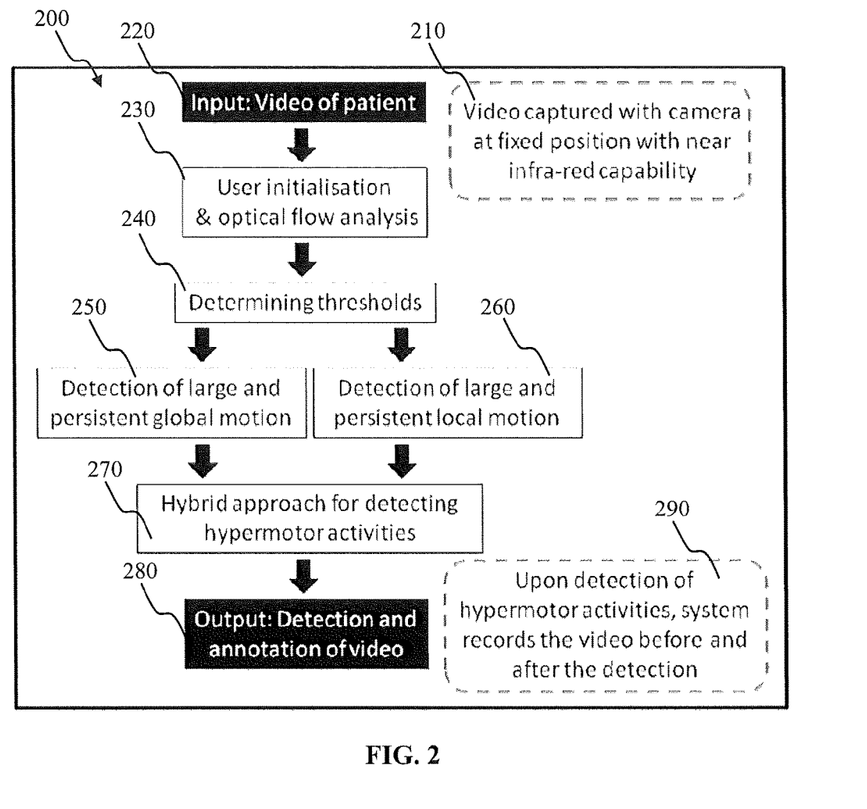
FIG. 2 illustrates a process flow summary of a method for detecting hypermotor activity according to embodiments of the present disclosure.

FIG. 2 illustrates a process flow summary of a method for detecting hypermotor activity according to embodiments of the present disclosure. In embodiments, a system 100 can be provided, arranged to operate or function based on such a method according to embodiments of the present disclosure. System 100 can be configured to utilize spatio-temporal information of optical flow, and perform a detection based on the magnitude of the flow fields identified. In embodiments, a camera 110 is provided as part of the system, the camera configured to capture video imaging of the patient under monitoring. Method 200 can be a method of detecting hypermotor activity in a patient. In 210, camera 110 can be used to capture video. In embodiments, video can be captured with camera 110 at a fixed position with near infra-red capability.

In 220, the video captured by the camera 110 is provided to processing system 130. Video is provided in the form of digital information received as input in the processing system 130. At 230, user initialization of the system can take place. System 100 can prompt a user to select a region of the captured video to be analyzed. In embodiments, the full video can be analyzed. In embodiments, for example, when a patient is sleeping on a bed, the video input region can be limited to the patient on the bed. Allowing for selection of a region, background motion present in the scene can be reduced. This is useful as the present system is targeted at monitoring patients in constrained and unsupervised situations. Selecting a region limits that the motion detected can be considered to originate mainly from the patient. In selecting a region, a region selection module of the processing system can be configured to receive the user input selection and manipulate the digital information to operate based on user input selection.

In embodiments, the selected region can be of a predetermined size. In such a case, user overlays such a region selection on the video input. In embodiments, the selected region can be of a size of 320×256 pixels. Further, at 230, optical flow analysis can be carried out with an optical flow module in the processing system. According to embodiments, optical flow fields are calculated. In embodiments, the flow field of the current frame is calculated as the mean flow field with respect to a number of preceding frames. In embodiments, the flow field of the current frame is calculated as the mean flow field of the past $t_o=15$ frames. In embodiments, $t_o$ can be any other suitable number to obtain a smooth optical flow field, which can contribute to the removal of noise which can affect the performance of the present system.

At 240, thresholds for use in identifying motion are determined. In embodiments, the processing system can include a threshold determination module to carry out such a function. In embodiments, the thresholds relate to determination of a global motion and a local motion. In embodiments, the thresholds affect detection scores for a global motion and a local motion. Details on the determination of respective global motion threshold and local motion threshold will be provided later in the document.

At 250, the method can include carrying out a detection of large and persistent global motion based on the video input with a global motion analysis module in the processing system. At 260, the method can include carrying out a detection of large and persistent local motion based on the video input with a local motion analysis module in the processing system. At 270, the method can include carrying out of a hybrid approach in detecting hypermotor activities with a hypermotor activity analysis module. The above determinations will be elucidated further in the document.

At 280, the method provides an output being the detection of hypermotor activity, based on the video processing carried out by the processing system. The hypermotor activity analysis module can provide a determination of an activity detection and output accordingly, for example, to a supervisory system which can alert a responsible caretaker for immediate assistance. Further, at 280, annotation of video can be carried out in the method. Annotation of video can be carried out by a video annotation module in the processing system, or can be carried out by a supervisory system coupled to the hypermotor activity detection system 100.

At 290, the method can include post-processing. Method 200 can direct system 100 to carry out post-processing activity. Upon detection of hypermotor activity, system 100 can record video before and after the detection. In embodiments, a recording module in the processing system of the system 100 can be configured to record a predetermined number of frames before and after the detection. In embodiments, the recording module can be configured to record thousands of frames of video.

Detection of large persistent global motion will now be discussed in the framework of a hypermotor activity detection system. Processing system of the hypermotor activity detection system can include a global motion analysis module to carry out a detection of large persistent global motion. Global motion can be understood to be the motion present between entire video frames. Video frames can be understood to be a singular static display of pixels in a video input region. Such a region can be user-identified, as described above, or can include the raw video capture resolution.

In determining global motion, the optical flow field analysis is utilized. In embodiments, $F_{x,t_c}(i,j)$ and $F_{y,t_c}(i,j)$, the x and y components of the smoothed flow field for the current frame $t_c$ at pixel $\{i, j\}$ are considered. The global flow magnitude $G_{t_c}$ is then defined as:

$$G_{t_c} = \sum_{i,j} g_{t_c}(i,j) \quad (1)$$

$$G_{t_c} = \sum_{i,j} (\|F_{x,t_c}(i,j)\| + \|F_{y,t_c}(i,j)\|)$$

where $g_{t_c}(i,j)$ is the measure of motion present at each pixel $\{i, j\}$ in the frame $t_c$, and $G_{t_c}$ is a measure of the motion present in the current frame $t_c$. When $G_{t_c}$ is large, it implies that large movements are present. In embodiments, the system seeks to observe for large and persistent motion, since sudden large movements could be caused by the patients waking up or moving around, while hypermotor activities tend to result in large and persistent motion.

To avoid false detections caused by large movements over a short period of time, the probability that large global motion is present can be calculated by comparing $G_{t_n}$ for each of the past $N_F$ frames of $t_c$ with a global threshold $\tau_G$, where $t_n=t_c-N_F+1, \ldots, t_c$. In embodiments, there is provided an assumption that there are M frames with $G_{t_n}>\tau_G$. The probability that large global motion is present at $t_c$, obtained by observing the past $N_F$ frames, which can defined as a number of observation frames, can then be defined as:

$$P_{g,t_c} = \frac{M}{N_F} \quad (2)$$

where $P_{g,t_c}$ is the probability that large persistent motion is present. According to various embodiments, the motion between frames is assumed to be independent for simplicity. Such an arrangement can be similar to a nearest-neighbour voting framework, where past frames cast votes independently on the current frame's state. Subsequently, according to various embodiments, a global detection score $D_{g,t_c}$ is defined as:

$$D_{g,t_c} = \frac{\sum_{t_n=t_c-N_D+1,\ldots,t_c}^{t_c} P_{g,t_n}}{N_D} \quad (3)$$

where $D_{g,t_c}$ is the mean of $P_{g,t_n}$ over the past $N_D$ frames, which can defined as a number of detection frames, and $t_n=t_c-N_D+1, \ldots, t_c$. It is noted that $D_{g,t_c}$ is calculated over an observation period. This arrangement can lead to an understanding that large values of $D_{g,t_c}$ would indicate the presence of large and persistent global motion in the video. In embodiments, the global motion analysis module of the hypermotor activity detection system can provide a determination or a detection of hypermotor activity with regard to a global motion perspective based on the global detection score $D_{g,t_c}$.

In embodiments, the hypermotor activity detection system can include a processing system for the processing of video information captured of a patient, the processing system can further include a local motion analysis module to carry out a detection of local motion. Local motion can refer to the motion present in a local region or identified space of the video. The local motion analysis module can further include a local motion reference module configured to carry out a determination of activity detection based on large local motion, and a local motion persistence module configured to carry out a determination of persistent motion in local regions.

Figure 3:
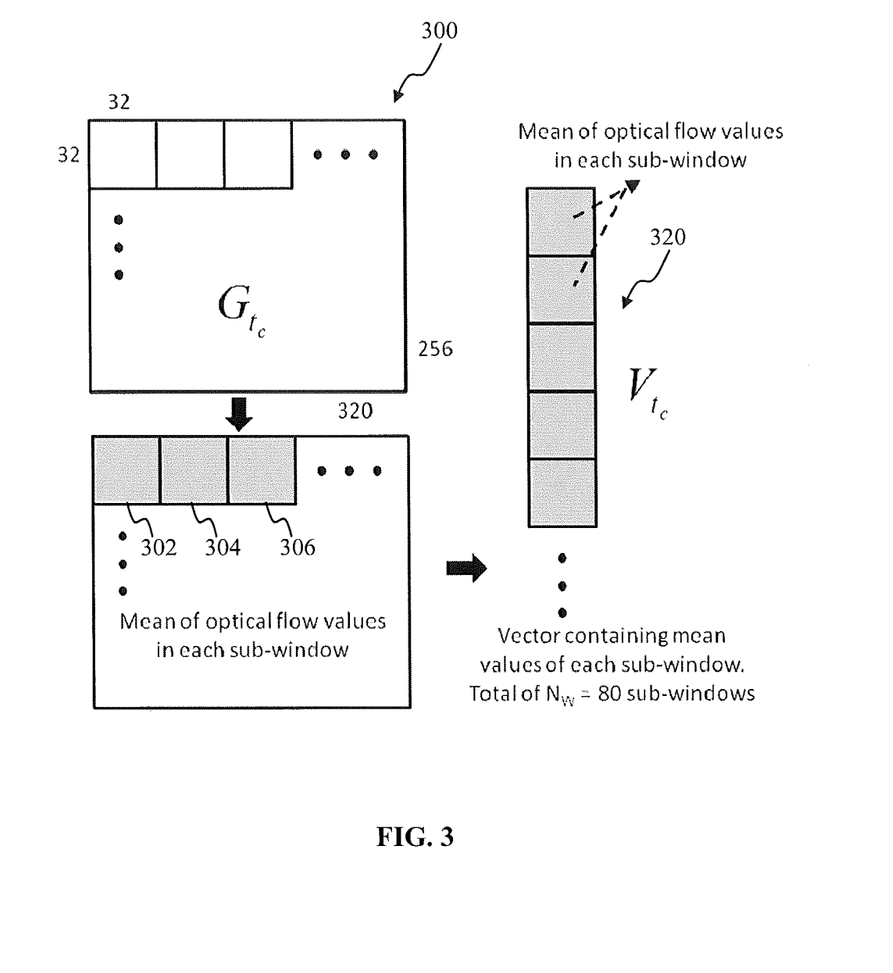
FIG. 3 illustrates the division of a video input region into sub-portions according to an embodiment.

In embodiments, the video input region is divided into various sub-portions to determine local motion. FIG. 3 illustrates the division of a video input region 300 into sub-portions according to an embodiment. In embodiments, the video input region 300, used to determine global motion, can be divided into various sub-portions with a division module in the system. In embodiments, the flow magnitude $g_{t_c}$, which can also be understood to be a flow field magnitude of the video input region, and as identified in Equation (1) is split into sub-windows 302, 304, 306. In embodiments, the flow magnitude $g_{t_c}$ is split into sub-windows of size 32×32 pixels. Sub-windows 302, 304, 306 can further be identified accordingly with respect to the sub-window location of the video input region. According to embodiments, a sub-window flow module can be provided to determine a sub-window flow field magnitude for each of the sub-windows. The mean flow magnitude of each sub-window can then be calculated.

According to various embodiments, flow magnitude $g_{t_c}$, which has been divided into flow magnitudes of different sub-regions, can also be represented by a feature vector $V_{t_c}$ 320, which contains the mean magnitudes of each sub-window 302, 304, 306. Feature vector 320 can be a column vector and can have dimensions $N_W \times 1$, where $N_W$ is the number of sub-windows. In various embodiments, where the dimension of the video input region can be 320×256 pixels, and the sub-window size is 32×32 pixels, the feature vector 320 can include a column vector with dimensions $N_W = 80$.

In embodiments, a local motion magnitude module can be provided as part of the processing system, the local motion magnitude module configured to obtain a magnitude of local motion based on the sub-window flow field magnitude. The magnitude of local motion can be represented by $W_{t_c}$. In embodiments, the magnitude of local motion $W_{t_c}$ can be defined here as the mean of $V_{t_c}$.

In embodiments, magnitude of local motion $W_{t_n}$ of the past $N_F$ frames of $t_c$ can be compared, with a local motion comparison module, with a local motion threshold $\tau_W$ where $t_n = t_c - N_F + 1, \ldots, t_c$. Further, the local motion reference module can calculate local motion reference value $P_{w,t_c}$ similar to (2), i.e. where $P_{w,t_c} = M/N_F$. Local motion reference value $P_{w,t_c}$ can be also understood to be the probability that large local motion is present. According to various embodiments, M can be the number of frames over the past $N_F$ frames for which $W_{t_n} > \tau_W$.

According to various embodiments, a local motion detection score $D_{w,t_c}$ can be defined as:

$$D_{w,t_c} = \frac{\sum_{t_n = t_c - N_D + 1, \ldots, t_c}^{t_c} P_{w,t_n}}{N_D} \qquad (4)$$

where $D_{w,t_c}$ is calculated over the past $N_D$ frames, such that large values of $D_{w,t_c}$ would indicate the presence of large local motion.

In embodiments, the hypermotor activity detection system further provides an analysis for the persistence of motion in a local region. In embodiments, processing system can include a local motion persistence module is provided to define a measure for the persistence of motion in a local region. Such an arrangement can allow the detection of hypermotor activities accurately and reliably.

In an embodiment, local motion persistence module can include a sub-window sorting module. Sub-window sorting module can be configured to consider or identify K sub-windows with the largest flow magnitudes. Further, sub-window sorting module can be configured to consider or identify K sub-windows with the largest flow magnitudes in the past $N_F$ frames. In identifying the K sub-windows, the sub-window with the largest sub-window flow field magnitude can be identified. In embodiments, the sub-windows can be sorted based on the sub-window flow field magnitude of each sub-window. In embodiments, K sub-windows with the largest flow magnitudes can be identified in a given frame.

Figure 4:
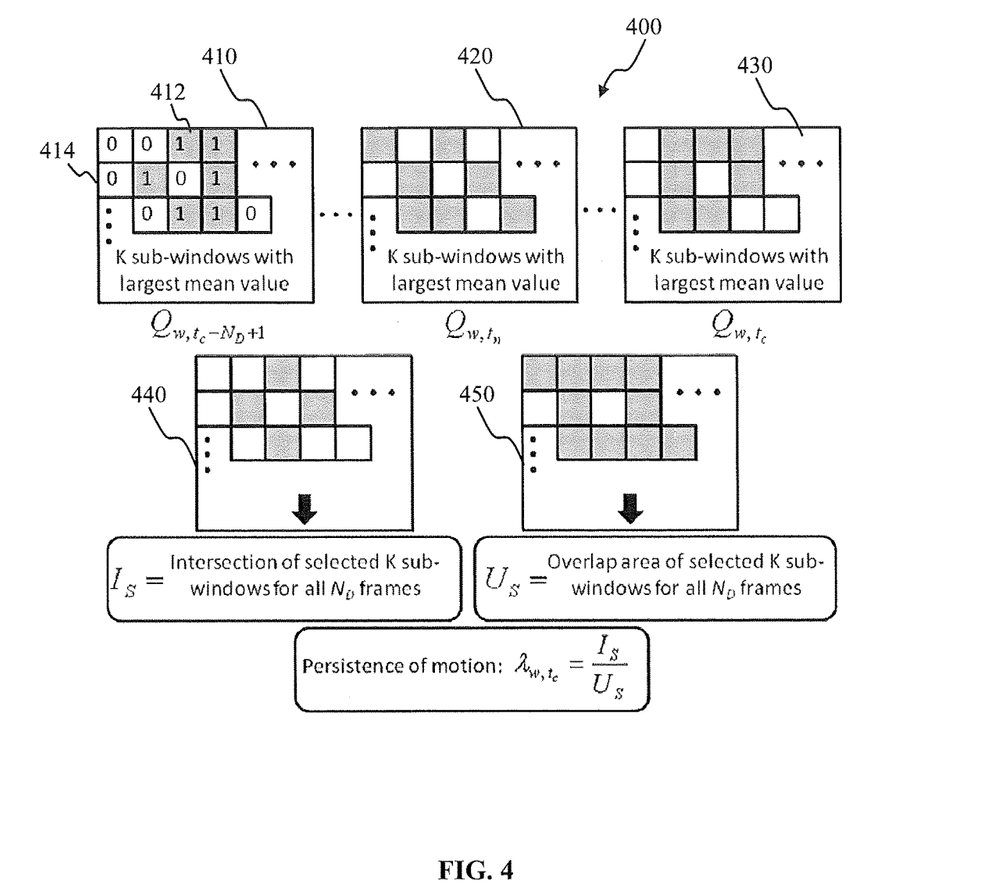
FIG. 4 illustrates a sequence of divided video input regions in determining a persistence of local motion.

FIG. 4 illustrates a sequence 400 of divided video input regions in determining a persistence of local motion. 410 shows a video input region divided into sub-windows and identifying a peak $Q_{w,t_c}$ map. A plurality of peak maps can be formed by a peak map module in the local motion persistence module. FIG. 4 illustrates peak maps formed for various frames, with map 410, 420 and 430 extracted for example. Peak map 410 can be provided for frame $Q_{w,t_c - N_D + 1}$, peak map 420 can be provided for frame $Q_{w,t_n}$, and peak map 430 can be provided for frame $Q_{w,t_c}$.

In general peak map $Q_{w,t_c}$ can be formed from the mean of $V_{t_n}$ over the past $N_F$, which is defined as:

$$V_{\mu,t_c} = \frac{\sum_{t_n = t_c - N_F + 1, \ldots, t_c}^{t_c} V_{t_n}}{N_F} \qquad (5)$$

where $t_c$ is the current frame, $t_n = t_c - N_F + 1, \ldots, t_c$, such that pixels 412 belonging to the K sub-windows with largest flow magnitudes in $V_{\mu,t_c}$ have a binary value of 1, and the remaining pixels 414 have a binary value of 0. Thus, peak map $Q_{w,t_c}$ can be understood to be an indication of local regions with large motion. Similar to the probability $P_{w,t_c}$ that large local motion is present, the past $N_D$ peak maps of $t_c$ are considered and thereafter the persistence score $\lambda_{w,t_c}$ is calculated as:

$$\lambda_{w,t_c} = \frac{I_S}{U_S} \qquad (6)$$

$$I_S = \sum_{i,j} (Q_{w, t_c - N_C + 1}(i,j) \cap \ldots \cap Q_{w,t_c}(i,j))$$

$$U_S = \sum_{i,j} (Q_{w, t_c - N_D + 1}(i,j) \cup \ldots \cup Q_{w,t_c}(i,j))$$

where $Q_{w,t_n}$ is a peak map and $t_n = t_c - N_D + 1, \ldots, t_c$. $I_S$ is the number of pixels in local regions which intersect across $N_D$ frames and can be shown in map 440. $U_S$ is the total overlapping area of all the pixels considered in the K sub-windows and can be shown in map 450. Persistence score $\lambda_{w,t_c}$ can be a measure of local regions with large and persistent motion, and it varies in the range of 0 . . . 1. When $\lambda_{w,t_c}$ is large, it can be understood that persistent local motion is present.

In embodiments, in detecting hypermotor activity, the hypermotor activity detection system utilizes a hybrid approach of determining activity based on global motion as well as local motion. In embodiments, detection is based on a consideration of the global motion detection score $D_{g,t_c}$ and the local motion detection score $D_{w,t_c}$. In embodiments, detection is based on a consideration of the global motion detection score $D_{g,t_c}$, the local motion detection score $D_{w,t_c}$, and the local motion persistence score $\lambda_{w,t_c}$. In embodiments, the hypermotor activity detection system can detect hypermotor activity based on only global motion or only local motion, or only local motion persistence, or any combination therefrom. In embodiments, the overall detection score is defined as:

$$D_{t_c} = w_1 D_{g,t_c} + w_2 D_{w,t_c} + w_3 \lambda_{w,t_c} \quad (7)$$

where $w_1$ is a weight or parameter for the global detection score, $w_2$ is a weight for the local detection score and $w_3$ is a weight for the intersection score. According to various embodiments, when $D_{t_c} > 0.9$, a detection is triggered. Depending on the desired accuracy or any other considerations, the trigger level can be varied. In embodiments, the parameters are weighed unevenly. In various embodiments, the values for the weights or parameters can be provided as $w_1=0.2$, $w_2=0.5$ and $w_3=0.3$. Such values have been determined by the present inventors as being relatively effective in the determination of hypermotor activity. Particularly, the inventors have identified that persistent local motion provides a very useful insight in detecting hypermotor activities and as such have provided higher weights to $D_{w,t_c}$ and $\lambda_{w,t_c}$ in various embodiments.

It can be understood that a good hypermotor activity detection system should have high detection accuracy, low false positive rates and low miss rates. The present inventors have paid careful attention to determining several important parameters which can affect the performance of the hypermotor activity detection system. Firstly, the thresholds $\tau_G$ and $\tau_W$ affect the detection scores $D_{g,t_c}$ and $D_{w,di\ c}$. Larger thresholds would typically result in lower detection scores, thus decreasing the false alarm rate of the system at the risk of higher miss rates. To determine $\tau_G$ and $\tau_W$, the threshold $\tau_G$ can be defined as:

$$\tau_G = \mu_{g,t_{N_\tau}} + 0.5\sigma_{g,t_{N_\tau}} \quad (8)$$

where $\mu_{g,t_{N_\tau}}$ is the mean and $\sigma_{g,t_{N_\tau}}$ is the standard deviation $G_{t_n}$ for $N_\tau$ frames after the system is initialized. According to various embodiments, the mean and standard deviation can be calculated over the range of frames $t_n = t_o+1, t_o+2, \ldots, N_\tau+t_o$, where $t_o=15$ is the number of frames required to initialise the algorithm, as discussed previously. In embodiments, threshold $\tau_W$ can be calculated with the mean and standard deviation of $W_{t_n}$ for $N_\tau$ frames, as defined in Equation (8). In embodiments, the number of frames $N_\tau$ is set to 150 frames. Other values are also possible.

In various embodiments, a minimum value can be specified by users for each threshold. This can allow the user to control the performance of the hypermotor activity detection system. In embodiments, the final thresholds can be determined as the maximum between the learnt threshold as derived using Equation (8) and the user-specified threshold.

In various embodiments, the thresholds $\tau_G$ and $\tau T_W$ can be determined once and used repeatedly during operation of the detection system. In embodiments, the thresholds $\tau_G$ and $\tau_W$ can undertake an adaptive learning strategy, where the system can review and relearn threshold values after a predetermined number of processed frames, as long as no detection is determined.

Further, apart from $\tau_G$ and $\tau T_W$, the number of observation frames $N_F$ in Equation (2) also affects the system's performance. When $N_F$ is large, the detection system is less sensitive to noise, possibly caused by natural movements of patients or caregivers in the video input. However, this can also lead to higher miss rates. In contrast, when $N_F$ is small, the system can have lower miss rates, but may be more prone to false alarms. According to various embodiments, operating the detection system with values of where $N_F=300$ and $N_D=30$ can produce accurate and reliable detections.

Advantageously, the hypermotor activity detection system according to various embodiments can operate to produce very low miss rates (≈0) due to the risk of SUDEP associated with unwitnessed hypermotor seizures. Concurrently, the detection system can be operated to produce low false alarm rates as well, since this would result in disturbances to caregivers of patients when alarms are triggered wrongly. In embodiments, when a detection is triggered, the detection system can records the previous 3000 frames and the next 3000 frames. Such a determination can translate to where the hypermotor activity detection system would record data to a supervisory system over a period of approximately seven minutes, at a frame rate of approximately 15 fps. To reduce the number of detections triggered for each seizure, a buffer of 900 frames can be provided between successive detections.

In embodiments, in operation, the detection system can provide a dual-mode of operation, one for the observation of hypermotor activities, and another for detection of hypermotor activity. In embodiments, observation of hypermotor activity is carried out with lower thresholds in learnt adaptively for recording of these activities without triggering alarms. In embodiments, detection of hypermotor activities is carried out with higher thresholds for the triggering of alarms. In embodiments, observation of hypermotor activities is carried out with lower thresholds learnt adaptively with $N_F=60$ for recording of these activities without triggering alarms, and detection of hypermotor activities with $N_F=300$ for higher thresholds for the triggering of alarms.

Experimental Data

In carrying out experimentation in determining the performance of a hypermotor activity detection system according to various embodiments, the system evaluated or processed 208 hours of test videos from 11 patients, with 22 hypermotor events and a total of 25 hypermotor seizures on EEG records. Continuous 8 hour epochs of activity were selected for testing, comprising of periods where the patient could be awake, sleeping or having a seizure. True electroclinical seizures were established by manual analysis of the recordings (True Seizures). Seizures detected by the system were recorded (system detections). To determine the sensitivity, all True Seizures were compared to the system detections. True Seizures with system detection were classed as True Positives. True Seizures without system detection of the seizures were classed as False Negatives. Sensitivity was calculated as a percentage: the True Positives over the total (True Positives+False Negatives). Automated detection with this system correctly identified 22 out of 25 true seizures (sensitivity 88%). Average latency from seizure onset to classification as seizure was 25.2 seconds.

There were 229 detections not associated with a True Seizure (False Positives, or FP). Of these, 107 were due to interference from other people entering the room and interacting with the patient—a supervised situation—and were excluded. Twenty three occurred during daytime recordings and 40 in the night prior to sleep onset. Fifty nine events occurred from sleep or during sleep. The False Positive rate occurring during the sleep phase when the caregiver is expected to be asleep was 0.28 FP per hour.

Such criterion ensures that the tests are performed under realistic operating conditions such as for operating a hypermotor activity detection system designed for long-term unsupervised monitoring.

Of the 41 seizures, 8 were excluded from consideration due to missing video data caused by technical issues. 9 other seizures were also excluded, which were not hypermotor seizures. These seizures were either hypomotor seizures or short seizures (i.e. lasting for less than 10 seconds), which did not belong to the target category of hypermotor seizures in the undertaken experimentation.

In addition, the test videos were selected to simulate realistic operating conditions expected of the proposed system, where the patient is alone and unsupervised. Specifically, the patient could either be awake and active, or the patient could be asleep. 2 measures were defined to study the performance of the hypermotor activity detection system:

$$D_R = \frac{D_{True}}{D_{Time} + N_{Miss}} \quad (9)$$

$$FP_R = \frac{D_{False}}{T} \quad (10)$$

where $D_R$ is the detection accuracy or sensitivity, $D_{True}$ is the number of detections which are actual seizures as verified by clinicians through EEG records and $N_{Miss}$ is the number of actual seizures which were missed. $FP_R$ is the false positive rate which measures the average number of false alarms per hour, $D_{False}$ is the number of false alarms and T is the time (in hours) of the test sequence. Here, we highlight that $D_{True}+N_{Miss}$ can be the total number of actual seizures as verified through EEG records. In addition, the latency between the onset of a seizure (as verified through EEG records) and detection by the system is also measured. To evaluate the system's performance, a currently available motion detection system including a marker-less motion detection algorithm (K. Cuppens, L. Lagae, B. Ceulemans, S. V. Huffel, and B. Vanrumste, "Automatic video detection of body movement during sleep based on optical flow in pediatric patients with epilepsy," Medical and Biological Engineering and Computing, vol. 48, no. 9, pp. 923-931, 2010) as described previously was used for performance comparison.

A summary of the obtained experimental results is shown in Table I. Overall, it can be observed that the present hypermotor activity detection system performed better than the currently available system even though they achieved the same detection accuracy $D_R$ of 91.7%, since the present system obtained a lower $FP_{False}$ of 0.59 than the 1.62 of the currently available system.

TABLE I

Comparison of Test Performance

| | $D_R$ (%) | $FP_R$ (per hour) | Latency (seconds) |
|---|---|---|---|
| Present system | 88 | 0.28 | 25.7 |
| Currently available system | 88 | 0.48 | 18.8 |

This can imply that the present system according to various embodiments is generally more robust to false alarms than the currently available system, and as such would be more feasible as a long-term unsupervised monitoring solution.

As a further note, even though the currently available system has a lower average detection latency of 18.8 s than the 25.7 s of the present system, it is highlighted that the average detection latencies of both systems would generally allow caregivers to provide a timely response in an unsupervised monitoring system.

Even though the monitoring solution is designed for monitoring pediatric patients, the system can be extended to patients of other age groups. In addition, the monitoring solution could also be extended to a generic sleep monitoring solution, since the present system seeks to detect anomalies in the motion of the scene.

Figure 5:
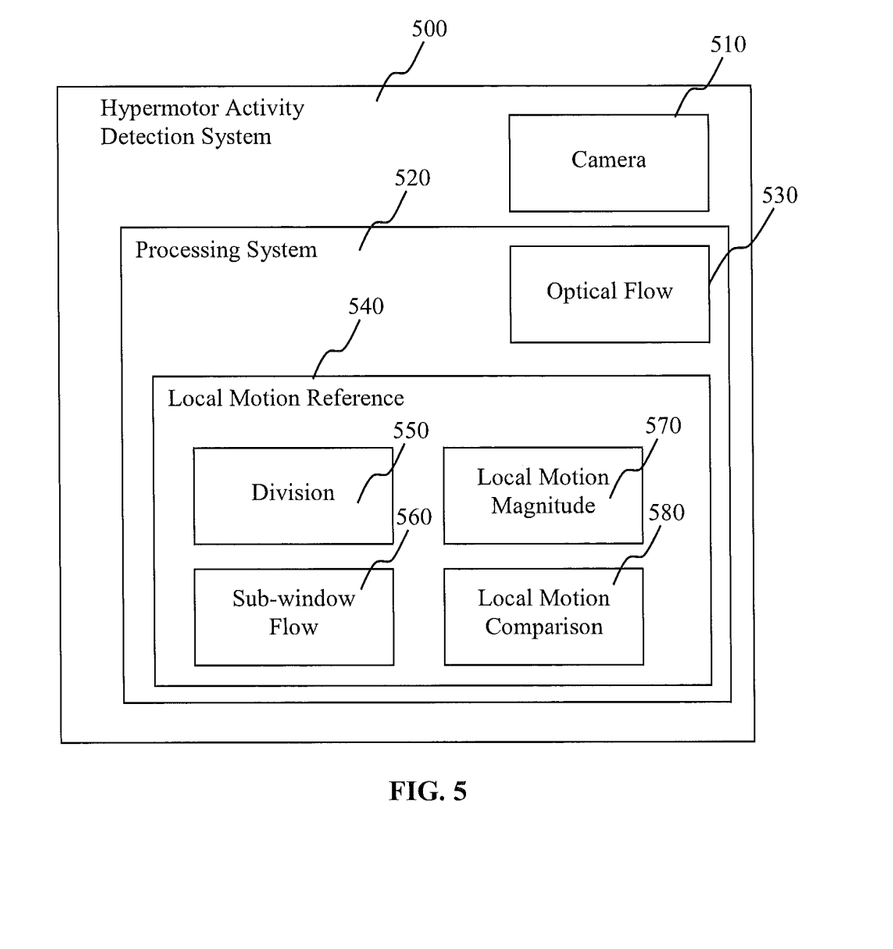
FIG. 5 illustrates a schematic of a hypermotor activity detection system according to an embodiment.

FIG. 5 illustrates a schematic of a hypermotor activity detection system according to an embodiment. According to various embodiments in the present disclosure, there is provided a hypermotor activity detection system 500. System 500 can include a video capture device 510 configured to monitor a patient and obtain a video input. System 500 can also include a processing system 520 configured to process the video input. Processing system 520 can include an optical flow module 530 configured to carry out an optical flow analysis on a video input region determined from the video input, and further determine a flow field magnitude of the video input region. Processing system 520 can also include a local motion reference module 540 which can include a division module 550 configured to divide the video input region into a plurality of sub-windows; a sub-window flow module 560 configured to determine a sub-window flow field magnitude for each of the plurality of sub-windows; a local motion magnitude module 570 configured to obtain a magnitude of local motion based on the sub-window flow field magnitude for each of the plurality of sub-windows; and a local motion comparison module 580 configured to compare the magnitude of local motion with a local motion threshold for a predetermined number of observation frames to obtain a local motion reference value.

In embodiments, the optical flow module is further configured to determine the flow field magnitude for a current frame of the video input.

In embodiments, any one of the flow field magnitude or the sub-window flow field magnitude is an average value of a preceding flow field calculation number of frames.

In embodiments, the local motion magnitude module is further configured to determine a feature vector based on the sub-window flow field magnitude for each of the plurality of sub-windows, and obtaining a mean of the feature vector, in obtaining a magnitude of local motion.

In embodiments, the feature vector is a column vector representing each of the sub-window flow field magnitudes for each of the plurality of sub-windows.

In embodiments, the local motion reference module is further configured to determine a local motion detection value over a predetermined number of detection frames based on the local motion reference value.

In embodiments, the local motion reference module is further configured to determine the local motion threshold based on a mean and standard deviation of the magnitude of local motion of the video input region.

In embodiments, the local motion reference module is further configured to determine the local motion threshold based on a mean and standard deviation of the magnitude of local motion of the video input region over a predetermined number of threshold frames.

In embodiments, the system further includes a sub-window sorting module configured to identify the sub-window with the largest sub-window flow field magnitude.

In embodiments, the sub-window sorting module is further configured to sort the sub-windows based on the sub-window flow field magnitude of each sub-window.

In embodiments, the sub-window sorting module is further configured to identify a predetermined number of sub-windows with the largest sub-window flow field magnitudes.

In embodiments, the sub-window sorting module is further configured to identify a predetermined number of sub-windows with the largest sub-window flow field magnitudes over the predetermined number of observation frames.

In embodiments, the system further includes a local motion persistence module configured to determine a peak map based on the identified sub-windows with the largest sub-window flow field magnitudes over the number of observation frames.

In embodiments, the local motion persistence module is further configured to obtain a plurality of peak maps over a detection number of preceding frames.

In embodiments, the local motion persistence module is further configured to determine a local motion persistence value based on the plurality of peak maps.

In embodiments, the local motion persistence module is further configured to determine an intersecting number of pixels which intersect across all of the plurality of peak maps.

In embodiments, the local motion persistence module is further configured to determine an overlapping number of all the pixels identified in the plurality of peak maps.

In embodiments, the local motion persistence module is further configured to obtain the ratio of the intersecting number of pixels and the overlapping number of pixels in determining the local motion persistence value.

In embodiments, the system further includes a global motion analysis module configured to determine a summation of the flow magnitude of each pixel in the video input region in determining the flow field magnitude of the video input region.

In embodiments, the system further includes a global motion reference module configured to determine a global motion reference value based on a comparison of the flow field magnitude of the video input region with a global motion threshold.

In embodiments, the global motion reference module is further configured to determine the global motion reference value based on a comparison of the flow field magnitude of the video input region with a global motion threshold over the predetermined number of observation frames.

In embodiments, the system further includes a global motion detection module configured to determine a global motion detection value over a detection number of preceding frames based on the global motion reference value.

In embodiments, the global motion analysis module is further configured to determine the global motion threshold based on a mean and standard deviation of the flow field magnitude of the video input region.

In embodiments, the global motion analysis module is further configured to determine the global motion threshold based on a mean and standard deviation of the flow field magnitude of the video input region over a threshold number of preceding frames.

In embodiments, the system further includes a hypermotor activity analysis module configured to detect hypermotor activity based on anyone of the parameters of a local motion detection value, a global motion detection value and a local motion persistence value.

In embodiments, the hypermotor activity analysis module is further configured to detect hypermotor activity based on a weighted combination of the parameters of a local motion detection value, a global motion detection value and a local motion persistence value.

In embodiments, the parameters are weighted unevenly.

In embodiments, the parameters are weighed in an order of heaviest first, local motion detection value, local motion persistence value, and global detection.

In embodiments, the hypermotor activity analysis module is further configured to determine a detection score based on the weighted combination of the parameters.

Figure 6:
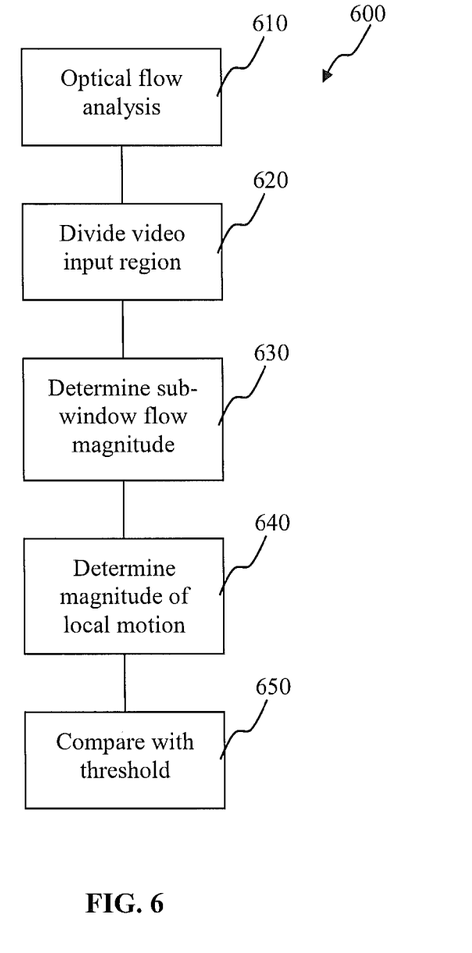
FIG. 6 illustrates a block schematic of a method according to an embodiment.

FIG. 6 illustrates a block schematic of a method according to an embodiment. Method 600 is provided, where method 600 can be a method for detecting hypermotor activity. At 610, the method can include carrying out an optical flow analysis on a video input region, including determining a flow field magnitude of the video input region. At 620, the method can include dividing the video input region into a plurality of sub-windows. At 630, the method can include determining a sub-window flow field magnitude for each of the plurality of sub-windows. At 640, the method can include obtaining a magnitude of local motion based on the sub-window flow field magnitude for each of the plurality of sub-windows. At 650, the method can include comparing the magnitude of local motion with a local motion threshold for a predetermined number of observation frames to obtain a local motion reference value.

In embodiments, the method further includes determining the flow field magnitude for a current frame of the video input.

In embodiments, the method further includes determining a feature vector based on the sub-window flow field magnitude for each of the plurality of sub-windows, and obtaining a mean of the feature vector, in obtaining a magnitude of local motion.

In embodiments, the feature vector is a column vector representing each of the sub-window flow field magnitudes for each of the plurality of sub-windows.

In embodiments, the method further includes determining a local motion detection value over a predetermined number of detection frames based on the local motion reference value.

In embodiments, the method further includes determining the local motion threshold based on a mean and standard deviation of the magnitude of local motion of the video input region.

In embodiments, the method further includes determining the local motion threshold based on a mean and standard deviation of the magnitude of local motion of the video input region over a predetermined number of threshold frames.

In embodiments, the method further includes identifying the sub-window with the largest sub-window flow field magnitude.

In embodiments, the method further includes sorting the sub-windows based on the sub-window flow field magnitude of each sub-window.

In embodiments, the method further includes identifying a predetermined number of sub-windows with the largest sub-window flow field magnitudes.

In embodiments, the method further includes identifying a predetermined number of sub-windows with the largest sub-window flow field magnitudes over the predetermined number of observation frames.

In embodiments, the method further includes determining a peak map based on the identified sub-windows with the largest sub-window flow field magnitudes over the number of observation frames.

In embodiments, the method further includes obtaining a plurality of peak maps over a detection number of preceding frames.

In embodiments, the method further includes determining a local motion persistence value based on the plurality of peak maps.

In embodiments, the method further includes determining an intersecting number of pixels which intersect across all of the plurality of peak maps.

In embodiments, the method further includes determining an overlapping number of all the pixels identified in the plurality of peak maps.

In embodiments, the method further includes obtaining the ratio of the intersecting number of pixels and the overlapping number of pixels in determining the local motion persistence value.

In embodiments, the method further includes determining a summation of the flow magnitude of each pixel in the video input region in determining the flow field magnitude of the video input region.

In embodiments, the method further includes determining a global motion reference value based on a comparison of the flow field magnitude of the video input region with a global motion threshold.

In embodiments, the method further includes determining the global motion reference value based on a comparison of the flow field magnitude of the video input region with a global motion threshold over the predetermined number of observation frames.

In embodiments, the method further includes determining a global motion detection value over a detection number of preceding frames based on the global motion reference value.

In embodiments, the method further includes determining the global motion threshold based on a mean and standard deviation of the flow field magnitude of the video input region.

In embodiments, the method further includes determining the global motion threshold based on a mean and standard deviation of the flow field magnitude of the video input region over a predetermined number of threshold frames.

In embodiments, the method further includes detecting hypermotor activity based on anyone of the parameters of a local motion detection value, a global motion detection value and a local motion persistence value.

In embodiments, the method further includes detecting hypermotor activity based on a weighted combination of the parameters of a local motion detection value, a global motion detection value and a local motion persistence value.

In embodiments, the method further includes weighing the parameters unevenly.

In embodiments, the method further includes weighing the parameters in an order of, heaviest first, local motion detection value, local motion persistence value, and global detection.

In embodiments, the method further includes determining a detection score based on the weighted combination of the parameters.

According to various embodiments, there is provided at least one computer program product directly loaded into a non-transitory memory module of a digital computer provided in a hypermotor activity detection system of the present disclosure. The computer program product can include software code portions for performing the steps of a method according to an embodiment of the present disclosure when the at least one computer product is run on the at least one digital computer.

In embodiments, the computer program product, directly loaded into a non-transitory memory module of a digital computer provided in a hypermotor activity detection system, can include software code portions for performing a method for detecting hypermotor activity, the method including: carrying out an optical flow analysis on a video input region, including determining a flow field magnitude of the video input region; dividing the video input region into a plurality of sub-windows; determining a sub-window flow field magnitude for each of the plurality of sub-windows; and obtaining a magnitude of local motion based on the sub-window flow field magnitude for each of the plurality of sub-windows; and comparing the magnitude of local motion with a local motion threshold for a predetermined number of observation frames to obtain a local motion reference value.

The above apparatus, method and/or system as described and illustrated in the corresponding figures, is not intended to limit an or any apparatus, method or system as according to an embodiment, and the scope of the present disclosure. The description further includes, either explicitly or implicitly, various features and advantages of the method or system according to the present disclosure, which can be encompassed within an apparatus, method or system according to the disclosure.

While embodiments of the disclosure have been particularly shown and described with reference to specific embodiments, it should be understood by those skilled in the art that various changes in form and detail may be made therein without departing from the spirit and scope of the disclosure as defined by the appended claims. The scope of the disclosure is thus indicated by the appended claims and all changes which come within the meaning and range of equivalency of the claims are therefore intended to be embraced.

What is claimed is:

1. A hypermotor activity detection system, comprising:
a video capture device configured to monitor a patient and obtain a video input; and
a processing system configured to process the video input, comprising:
an optical flow module configured to carry out an optical flow analysis on a video input region determined from the video input, and further determine a flow field magnitude of the video input region;
a local motion reference module comprising:
a division module configured to divide the video input region into a plurality of sub-windows;

a sub-window flow module configured to determine a sub-window flow field magnitude for each of the plurality of sub-windows;

a local motion magnitude module configured to obtain a magnitude of local motion based on the sub-window flow field magnitude for each of the plurality of sub-windows; and a local motion comparison module configured to compare the magnitude of local motion with a local motion threshold for a predetermined number of observation frames to obtain a local motion reference value;

an output module configured to generate an output indicating the detection of hypermotor activity of the patient being monitored based on the obtained local motion reference value; and a video recording module to record one or more clips from the video input in response to the output indicating the detection of the hypermotor activity of the patient being monitored.

2. The hypermotor activity detection system of claim 1, wherein any one of the flow field magnitude or the sub-window flow field magnitude is an average value of a preceding flow field calculation number of frames.

3. The hypermotor activity detection system of claim 1, wherein the local motion magnitude module is further configured to determine a feature vector based on the sub-window flow field magnitude for each of the plurality of sub-windows, and obtaining a mean of the feature vector, in obtaining a magnitude of local motion.

4. The hypermotor activity detection system of claim 1, wherein the local motion reference module is further configured to determine a local motion detection value over a predetermined number of detection frames based on the local motion reference value.

5. The hypermotor activity detection system of claim 1, wherein the local motion reference module is further configured to determine the local motion threshold based on a mean and standard deviation of the magnitude of local motion of the video input region.

6. The hypermotor activity detection system of claim 1, further comprising a sub-window sorting module configured to sort the sub-windows based on the sub-window flow field magnitude of each sub-window.

7. The hypermotor activity detection system of claim 6, wherein the sub-window sorting module is further configured to identify a predetermined number of sub-windows with the largest sub-window flow field magnitudes.

8. The hypermotor activity detection system of claim 7, wherein the sub-window sorting module is further configured to identify a predetermined number of sub-windows with the largest sub-window flow field magnitudes over the predetermined number of observation frames.

9. The hypermotor activity detection system of claim 8, further comprising a local motion persistence module configured to determine a peak map based on the identified sub-windows with the largest sub-window flow field magnitudes over the number of observation frames.

10. The hypermotor activity detection system of claim 9, wherein the local motion persistence module is further configured to obtain a plurality of peak maps over a detection number of preceding frames.

11. The hypermotor activity detection system of claim 10, wherein the local motion persistence module is further configured to determine a local motion persistence value based on the plurality of peak maps.

12. The hypermotor activity detection system of claim 11, wherein the local motion persistence module is further configured to obtain the ratio of an intersecting number of pixels which intersect across all of the plurality of peak maps, and an overlapping number of all the pixels identified in the plurality of peak maps, in determining the local motion persistence value.

13. The hypermotor activity detection system of claim 1, further comprising a global motion reference module configured to determine a global motion reference value based on a comparison of the flow field magnitude of the video input region with a global motion threshold.

14. The hypermotor activity detection system of claim 13, further comprising a global motion detection module configured to determine a global motion detection value over a detection number of preceding frames based on the global motion reference value.

15. The hypermotor activity detection system of claim 13, further comprising a global motion analysis module configured to determine the global motion threshold based on a mean and standard deviation of the flow field magnitude of the video input region.

16. The hypermotor activity detection system of claim 1, further comprising a hypermotor activity analysis module configured to detect hypermotor activity based on a weighted combination of the parameters of a local motion detection value, a global motion detection value and a local motion persistence value.

17. The hypermotor activity detection system of claim 16, wherein the parameters are weighed in an order of, heaviest first, local motion detection value, local motion persistence value, and global detection.

18. The hypermotor activity detection system of claim 16, wherein the hypermotor activity analysis module is further configured to determine a detection score based on the weighted combination of the parameters.

19. The hypermotor activity detection system of claim 1, further comprising:

the video recording module to record a predetermined amount of video data from the video input before and after the detection of the hypermotor activity of the patient being monitored.

20. The hypermotor activity detection system of claim 19, wherein the predetermined amount of video data comprises a predetermined number of frames of video data before the detection of the hypermotor activity of the patient being monitored, and a predetermined number of frames of video data after the detection of the hypermotor activity of the patient being monitored.

21. The hypermotor activity detection system of claim 1, further comprising:

the video recording module to buffer a number of frames of video input after a first detection of hypermotor activity of the patient being monitored, and to combine the first detection of hypermotor activity of the patient being monitored with a second detection of hypermotor activity of the patient being monitored when the second detection occurs within the number of frames of video input in the buffer.

22. A computer-implemented method for detecting hypermotor activity, performed by one or more processors, the method comprising:

carrying out an optical flow analysis on a video input region determined from a video input of a patient being monitored, comprising determining a flow field magnitude of the video input region;

dividing the video input region into a plurality of sub-windows;
determining a sub-window flow field magnitude for each of the plurality of sub-windows;
obtaining a magnitude of local motion based on the sub-window flow field magnitude for each of the plurality of sub-windows;
comparing the magnitude of local motion with a local motion threshold for a predetermined number of observation frames to obtain a local motion reference value;
generating an output indicating the detection of hypermotor activity of the patient being monitored based on the obtained local motion reference value; and
recording one or more clips from the video input in response to the output indicating the detection of the hypermotor activity of the patient being monitored.

23. A computer program product directly loadable into a non-transitory memory module of a digital computer provided in a hypermotor activity detection system, the computer program product comprising instructions executable by one or more processors of the digital computer to perform a method for detecting hypermotor activity, the method comprising:

carrying out an optical flow analysis on a video input region determined from a video input of a patient being monitored, comprising determining a flow field magnitude of the video input region;
dividing the video input region into a plurality of sub-windows;
determining a sub-window flow field magnitude for each of the plurality of sub-windows;
obtaining a magnitude of local motion based on the sub-window flow field magnitude for each of the plurality of sub-windows; and
comparing the magnitude of local motion with a local motion threshold for a predetermined number of observation frames to obtain a local motion reference value;
generating an output indicating the detection of hypermotor activity of the patient being monitored based on the obtained local notion reference value; and
recording one or more clips from the video input in response to the output indicating the detection of the hypermotor activity of the patient being monitored.

* * * * *